(12) United States Patent
Goto (10) Patent No.: US 10,362,933 B2
(45) Date of Patent: Jul. 30, 2019

(54) OPHTHALMOLOGIC APPARATUS, TOMOGRAPHIC IMAGE GENERATION METHOD, AND PROGRAM THAT DETERMINE AN IMAGING REGION FOR CAPTURING A PLURALITY OF TOMOGRAPHIC IMAGES FOR GENERATING AN AVERAGED TOMOGRAPHIC IMAGE

(71) Applicant: CANON KABUSHIKI KAISHA, Tokyo (JP)

(72) Inventor: Atsushi Goto, Yokohama (JP)

(73) Assignee: Canon Kabushiki Kaisha, Tokyo (JP)

( * ) Notice: Subject to any disclaimer, the term of this patent is extended or adjusted under 35 U.S.C. 154(b) by 288 days.

(21) Appl. No.: 14/963,867

(22) Filed: Dec. 9, 2015

(65) Prior Publication Data

US 2016/0166143 A1 Jun. 16, 2016

(30) Foreign Application Priority Data

Dec. 16, 2014 (JP) ................. 2014-254597

(51) Int. Cl.
*A61B 3/10* (2006.01)
*A61B 3/00* (2006.01)
*A61B 3/113* (2006.01)
*A61B 3/14* (2006.01)
*G02B 27/48* (2006.01)

(52) U.S. Cl.
CPC ............ *A61B 3/0025* (2013.01); *A61B 3/102* (2013.01); *A61B 3/113* (2013.01); *A61B 3/14* (2013.01); *G02B 27/48* (2013.01)

(58) Field of Classification Search
CPC ......... A61B 3/12; A61B 3/145; A61B 3/1225; A61B 3/0025; A61B 3/14; A61B 3/102; A61B 3/113; A61B 3/1025; A61B 3/1233; A61B 3/1241; G02B 27/48
USPC ......................................................... 351/206
See application file for complete search history.

(56) References Cited

U.S. PATENT DOCUMENTS

| | | | | |
|---|---|---|---|---|
| 2011/0267581 A1* | 11/2011 | Nakajima | ............... | A61B 3/102 351/206 |
| 2012/0229761 A1* | 9/2012 | Makihira | ............... | A61B 3/102 351/206 |
| 2017/0273558 A1* | 9/2017 | Tamura | ................... | A61B 3/14 |

FOREIGN PATENT DOCUMENTS

| | | |
|---|---|---|
| JP | 2011-095005 A | 5/2011 |
| JP | 2013153793 A | 8/2013 |
| JP | 2013183909 A | 9/2013 |

* cited by examiner

*Primary Examiner* — William R Alexander
*Assistant Examiner* — Henry A Duong
(74) *Attorney, Agent, or Firm* — Canon U.S.A., Inc. IP Division (57) ABSTRACT

An ophthalmologic apparatus includes an error obtaining unit configured to obtain a value corresponding to a difference between a first imaging position which tracks a predetermined position of an eye portion under control of a tracking unit and the predetermined position, a determination unit configured to determine a position which is shifted from the first imaging position which tracks the predetermined position as a second imaging position in accordance with the value corresponding to the difference. The ophthalmologic apparatus averages tomographic images of the first and second imaging positions.

15 Claims, 9 Drawing Sheets

OPHTHALMOLOGIC APPARATUS, TOMOGRAPHIC IMAGE GENERATION METHOD, AND PROGRAM THAT DETERMINE AN IMAGING REGION FOR CAPTURING A PLURALITY OF TOMOGRAPHIC IMAGES FOR GENERATING AN AVERAGED TOMOGRAPHIC IMAGE

BACKGROUND

Field

Aspects of the present technique generally relate to an ophthalmologic apparatus, a tomographic image generation method, and a program.

Description of the Related Art

As an optical tomographic image obtaining apparatus which obtains a tomographic image of a living body and the like in a non-destructive manner or a non-invasive manner, a light interference tomographic image obtaining apparatus which is referred to as "optical coherent tomography (OCT)" has been used.

The OCT obtains a tomographic image using light. More specifically, a light beam reflected by a measurement target and a light beam emitted from a reference mirror interfere with each other, and data of wavelength dependency (more specifically, wavenumber dependency) of intensity of a light beam obtained by the interference is subjected to Fourier transform so that a tomographic image is obtained. Examples of such a light interference tomographic image obtaining apparatus include time domain OCT (TD-OCT) which obtains depth information of a measurement target by changing a position of a reference mirror, spectral domain optical coherence tomography (SD-OCT) utilizing a broadband light source, and swept source optical coherence tomography (SS-OCT) using a wavelength variable light source apparatus capable of changing an oscillation wavelength as a light source.

In the OCT, an image is generated utilizing light interference, and therefore, speckle noise is generated in a formed image. Japanese Patent Laid-Open No. 2011-95005 discloses a technique of obtaining tomographic images in positions intentionally shifted from a desired position on a fundus by a predetermined amount $\Delta Y$ and performing averaging between the obtained tomographic image and a tomographic image in the desired position so that speckle noise is reduced. Furthermore, the predetermined amount $\Delta Y$ may be set in accordance with an involuntary eye movement according to Japanese Patent Laid-Open No. 2011-95005.

However, in a case where an image of an eye having a large involuntary eye movement is to be captured, even if the amount $\Delta Y$ of the intentional shift of the positions of the imaging of the tomographic images is zero, although the speckle noise is reduced when obtained tomographic images are averaged, a resultant tomographic image blurs. Specifically, reduction of the speckle noise included in the tomographic image and reduction of the blur of the tomographic image are not simultaneously attained due to the involuntary eye movement.

SUMMARY

Accordingly, an aspect of the present invention simultaneously attains reduction of speckle noise included in a tomographic image and reduction of a blur of the tomographic image.

In addition, another aspect of the present invention provides operation effects which are obtained by configurations illustrated in an embodiment below and which may not be obtained by the related techniques.

Yet another aspect of the present invention provides an ophthalmologic apparatus including a detection unit configured to detect a movement of a subject's eye, a tracking unit configured to cause a first imaging position to track a predetermined position of the subject's eye in accordance with a result of the detection, an error obtaining unit configured to obtain a value corresponding to a difference between the first imaging position which tracks the predetermined position and the predetermined position, a determination unit configured to determine a position which is shifted from the first imaging position which tracks the predetermined position as a second imaging position in accordance with the value corresponding to the difference, a tomographic image obtaining unit configured to obtain tomographic images of the first and second imaging positions, and a generation unit configured to generate a tomographic image by averaging the tomographic images obtained by the tomographic image obtaining unit.

Further features of the present disclosure will become apparent from the following description of exemplary embodiments with reference to the attached drawings.

DESCRIPTION OF THE EMBODIMENT

An ophthalmologic apparatus according to an embodiment will be described with reference to the accompanying drawings. Configurations in the embodiment herein are merely examples, and the present invention is not limited to the examples described below.

Entire Configuration of Apparatus

Figure 1:
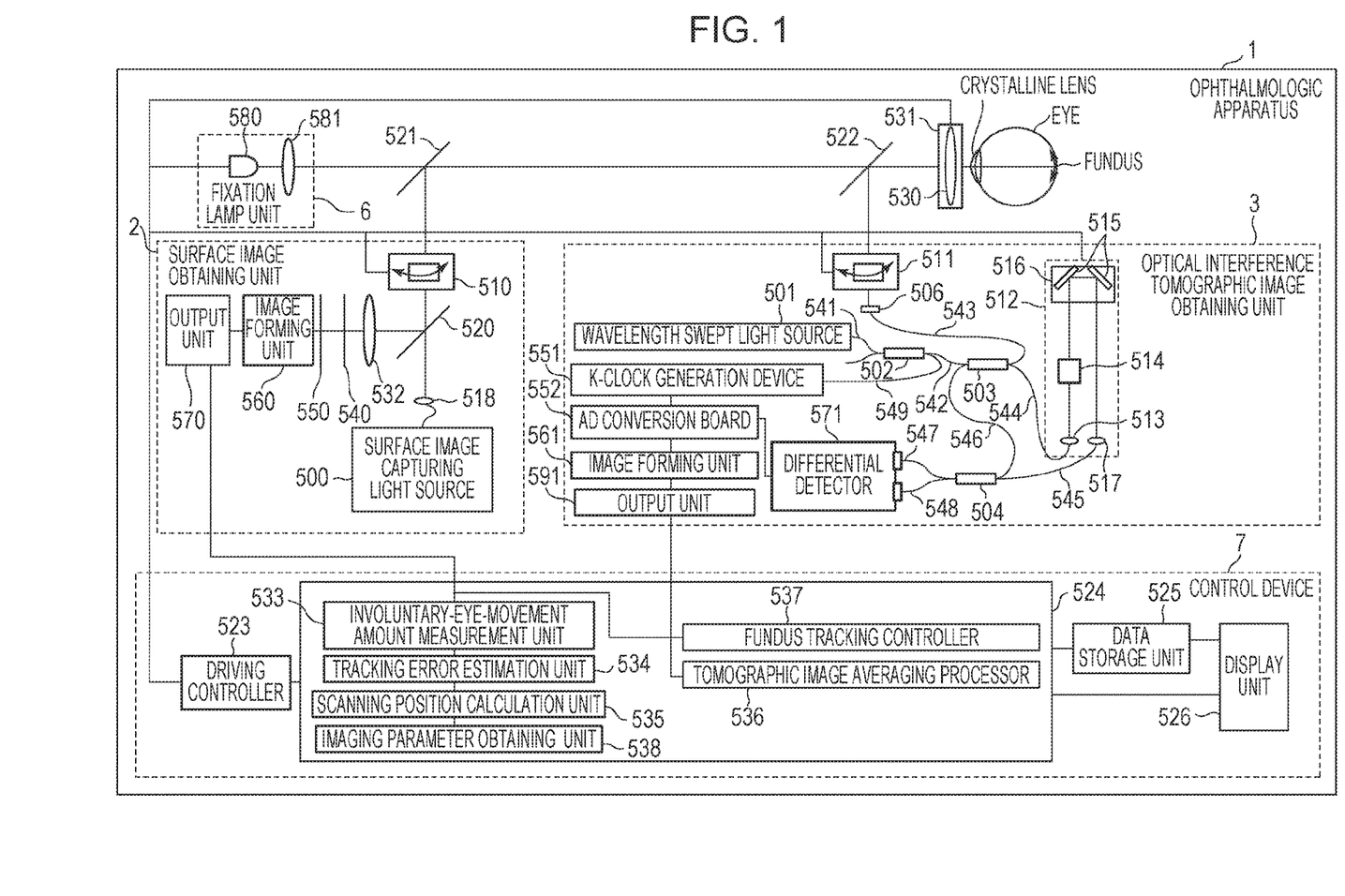
FIG. 1 is a diagram schematically illustrating an entire configuration of an ophthalmologic apparatus according to an embodiment.

FIG. 1 is a diagram schematically illustrating an entire configuration of an ophthalmologic apparatus 1 according to this embodiment. The ophthalmologic apparatus 1 includes a light interference tomographic image obtaining unit 3, a surface image obtaining unit 2, a fixation lamp unit 6, and a control device 7.

Light Interference Tomographic Image Obtaining Unit

The light interference tomographic image obtaining unit 3 captures an image of a tomographic image of an eye portion, and is constituted by a TD-OCT, an SD-OCT, or an SS-OCT. A configuration of the light interference tomographic image obtaining unit 3 which is an SS-OCT is illustrated in FIG. 1. Although the light interference tomographic image obtaining unit 3 is an SS-OCT in this embodiment, the present invention is not limited to this, and the light interference tomographic image obtaining unit 3 may be an SD-OCT or a TD-OCT.

A wavelength swept light source 501 emits light having a wavelength in a range from 994 nm to 1101 nm in a frequency of 100 kHz, for example. These numerical values are merely examples and other values may be employed. Light emitted from the wavelength swept light source 501 is guided through a fiber 541 to a fiber coupler 502 which divides the light into a light beam transmitted to a fiber coupler 503 through a fiber 542 and a light beam transmitted to a K-clock generation device 551 through a fiber 549. A branching rate of the fiber coupler 502 is 90:10 ((the light beam transmitted to the fiber coupler 503):(the light beam transmitted to the K-clock generation device 551)). The light beam transmitted to the fiber coupler 503 is divided into measurement light transmitted to a sample through a fiber 543 and reference light transmitted to a reference system 512 through a fiber 544. A branching rate of the fiber coupler 503 is 80:20 ((the reference light):(the measurement light)).

The measurement light is emitted through the fiber 543 from a collimator 506 as parallel light. The emitted measurement light reaches a dichroic mirror 522 through an X-Y scanning mirror 511 constituted by a galvanometer mirror which performs scanning on a fundus using the measurement light in a horizontal direction and a vertical direction. The X-Y scanning mirror 511 is an example of a scanning unit, and is controlled by a driving controller 523 so as to perform scanning on the fundus in a desired range using the measurement light. The range on the fundus scanned by the measurement light may be seen to be a range of obtainment of tomographic images, a position of obtainment of tomographic images, and a position of irradiation of the measurement light. The dichroic mirror 522 is characterized by reflecting light having wavelengths in a range from 990 nm to 1110 nm and allowing light of other wavelengths to pass. These numerical values are merely examples and other values may be employed.

The measurement light reflected by the dichroic mirror 522 is focused on retina layers of the fundus which is a subject by a focus lens 530 mounted on a stage 531. The measurement light emitted to the fundus is reflected and scattered by the retina layers, returns to the fiber coupler 503 through the optical path described above, and reaches a fiber coupler 504 through a fiber 546.

On the other hand, the reference light branched by the fiber coupler 503 is emitted through the fiber 544 from a collimator 513 as parallel light. The emitted reference light is reflected by mirrors 515 on a coherence gate stage 516 through a dispersion compensating glass 514 and reaches the fiber coupler 504 through a collimator 517.

The coherence gate stage 516 is controlled by the driving controller 523 so as to cope with differences among lengths of eyeballs of examinees. Note that the term "coherence gate" means a position in a light path of the measurement light which corresponds to a light path length of the reference light. Although the light path length of the reference light is changed in this embodiment, at least a difference between a length of the light path of the measurement light and a length of the light path of the reference light is changed.

The measurement light and the reference light which reached the fiber coupler 504 are combined with each other so that interference light (hereinafter also referred to as "combined light" where appropriate) is obtained, and the interference light is received by a differential detector 571.

Furthermore, the light branched by the fiber coupler 502 is transmitted to the K-clock generation device 551 which outputs trigger signals at a wavenumber equal interval.

The K-clock generation device 551 includes a Mach-Zehnder interferometer (MZI), a differential detector, and a comparator, for example, and outputs trigger signals at a wavenumber equal interval.

The combined light received by the differential detector 571 is converted into an electric signal to be sampled by an AD conversion board 552. Here, the AD conversion board 552 samples the combined light converted into the electric signal at the wavenumber equal interval in accordance with the trigger signals output from the K-clock generation device 551.

An image forming unit 561 performs signal processing, such as fast Fourier transform (FFT), on spectroscopic signals obtained at the wavenumber equal interval so as to obtain reflectance distribution in a depth direction of the sample. Furthermore, the X-Y scanning mirror 511 performs line scanning on the sample using the measurement light so as to obtain a 2D tomographic image to be output to an output unit 591.

Surface Image Obtaining Unit

The surface image obtaining unit 2 captures a surface image of the eye portion and is constituted by a fundus camera or scanning laser ophthalmoscopy (SLO), for example. In this embodiment, a case where the SLO is used as the surface image obtaining unit 2 is described as an example. Here, the surface image obtaining unit 2 is an example of a surface image obtaining unit which obtains surface images of a subject's eye.

A surface image capturing light source 500 is a semiconductor laser and emits light having a center wavelength of 780 nm, for example, in this embodiment. A value of the center wavelength is merely an example and other values may be employed. The measurement light emitted from the surface image capturing light source 500 is further emitted from a collimator 518 as parallel light, passes through a perforated portion of a perforated mirror 520, and reaches a dichroic mirror 521 through an X-Y scanning mirror 510 constituted by a galvanometer mirror which performs scanning in the horizontal direction and the vertical direction on the fundus using the measurement light. The X-Y scanning mirror 510 controlled by the driving controller 523 may perform scanning on the fundus in a desired range using the measurement light.

Note that the X-Y scanning mirror 510 is an example of a scanning unit for the SLO and may be formed as a common XY scanner. The dichroic mirror 521 is characterized by reflecting light having wavelengths in a range from 760 nm to 800 nm and allowing light having other wavelengths to pass. These numerical values are merely examples and other values may be employed.

The measurement light reflected by the dichroic mirror 521 reaches the fundus through an optical path the same as that of the light interference tomographic image obtaining unit 3.

The measurement light emitted to the fundus is reflected and scattered by the fundus and reaches the perforated mirror 520 through the optical path described above. The light reflected by the perforated mirror 520 is received by a photosensor 550 through a lens 532 and a diaphragm 540, converted into an electric signal, transmitted to the image forming unit 560, and output from an output unit 570 as image data. The photosensor 550 may be a photodiode or a photomultiplier tube, for example.

Here, a position of the perforated mirror 520 is conjugated with a position of a pupil of the subject's eye. In light obtained when the measurement light which is emitted to the fundus is reflected and scattered by the fundus, light which passes a pupil peripheral portion is reflected by the perforated mirror 520.

Fixation Lamp Unit

The fixation lamp unit 6 includes an internal fixation lamp display unit 580 and a lens 581. As the internal fixation lamp display unit 580, a plurality of light emitting diodes (LDs) is arranged in a matrix. Lighting positions of the light emitting diodes are changed depending on a portion to be imaged under control of the driving controller 523. Light emitted from the internal fixation lamp display unit 580 is guided to the subject's eye through the lens 581. The internal fixation lamp display unit 580 emits light having a wavelength of 520 nm and displays a desired pattern under control of the driving controller 523. These numerical values are merely examples and other values may be employed.

A wavelength of the light emitted from the internal fixation lamp display unit 580 may be 635 nm, and a wavelength of a color which is easily recognized by a patient may be selected from wavebands of visible light. That is, the wavelength of the light emitted from the internal fixation lamp display unit 580 is not limited to the values of this embodiment.

Control Device

The control device 7 includes the driving controller 523, a signal processing unit 524, a data storage unit 525, and a display unit 526.

Note that the control device 7 may be constituted by a personal computer (PC). In this case, functions of the driving controller 523 and the signal processing unit 524 included in the control device 7 are seen to be control programs, and control of the ophthalmologic apparatus 1 is realized when a CPU executes the control programs. Specifically, the CPU included in the control device 7 develops the programs stored in a ROM, not illustrated, in a RAM, not illustrated, and executes the programs so as to function as the driving controller 523 and the signal processing unit 524.

Note that only one CPU or a plurality of CPUs and only one storage unit or a plurality of storage units which store the control programs may be provided. That is, in a case where at least one processing system (the CPU) and at least one storage device (the ROM) are connected to each other and at least one processing apparatus executes the programs stored in at least one storage device, the ophthalmologic apparatus 1 functions as the driving controller 523 and the signal processing unit 524.

The driving controller 523 controls various portions of the ophthalmologic apparatus 1 including the X-Y scanning mirror 511 and the coherence gate stage 516 as described above.

The signal processing unit 524 includes an imaging parameter obtaining unit 538, an involuntary-eye-movement-amount measurement unit 533, a tracking error estimation unit 534, a scanning position calculation unit 535, a tomographic image averaging unit 536, and a fundus tracking control unit 537. Functions included in the signal processing unit 524 are also realized when the CPU executes the control program.

The imaging parameter obtaining unit 538 obtains imaging parameters of the OCT from an input by an operator using a user interface, such as a mouse or a keyboard, not illustrated.

The involuntary-eye-movement-amount measurement unit 533 performs measurement of an amount of an involuntary eye movement in accordance with an image signal output from the output unit 570 included in the surface image obtaining unit 2. In other words, the involuntary-eye-movement-amount measurement unit 533 obtains a movement of the subject's eye. Specifically, the involuntary-eye-movement-amount measurement unit 533 is an example of a detection unit which detects a movement of the subject's eye. A method for measuring an amount of an involuntary eye movement will be described in detail later.

The tracking error estimation unit 534 estimates a position error (hereinafter referred to as a "tracking error") obtained when an image of the subject's eye obtained by the output of the surface image obtaining unit 2 is captured by the light interference tomographic image obtaining unit 3. More specifically, the tracking error estimation unit 534 estimates a shift (a displacement) between an imaging position and a predetermined position in a case where the fundus tracking control unit 537, which will be described later, causes the imaging position of the light interference tomographic image obtaining unit 3 to track the predetermined position of the subject's eye. That is, the tracking error estimation unit 534 is an example of an error obtaining unit which obtains a value corresponding to a difference between a first imaging position which tracks the predetermined position of the eye portion under control of the fundus tracking control unit 537 (a tracking unit) and the predetermined position of the eye portion.

The scanning position calculation unit 535 calculates an OCT scanning position in accordance with the tracking error.

The tomographic image averaging unit 536 averages tomographic images in accordance with an image signal output from the output unit 591 included in the light interference tomographic image obtaining unit 3.

The fundus tracking control unit 537 causes the light interference tomographic image obtaining unit 3 to perform fundus tracking in accordance with a result of the measurement of the involuntary-eye-movement-amount measurement unit 533. Specifically, the fundus tracking control unit 537 is an example of a tracking unit which causes the first imaging position to track the predetermined position of the subject's eye in accordance with a result of the detection of a movement of the subject's eye. Note that the light interference tomographic image obtaining unit 3 obtains tomographic images under control of the fundus tracking control unit 537.

The obtainment of the imaging parameters, the measurement of an amount of an involuntary eye movement, the estimation of a tracking error, the calculation of a scanning position, the fundus tracking, the tomographic image averaging process, and the like will be described in detail hereinafter.

The data storage unit 525 stores images formed by the surface image obtaining unit 2 and the light interference tomographic image obtaining unit 3, image data subjected to the signal processing performed by the signal processing unit 524, and a result of the signal processing. The data storage unit 525 is constituted by a magnetic disc, for example. However, the data storage unit 525 is not limited to a magnetic disc.

The display unit 526 displays the images formed by the surface image obtaining unit 2 and the light interference tomographic image obtaining unit 3, the image data subjected to the signal processing performed by the signal processing unit 524, the result of the signal processing, other image data stored in the data storage unit 525, and results of the signal processing performed on the other image data.

The display unit 526 is a liquid crystal display, for example.

Scanning Positions

Figure 2:
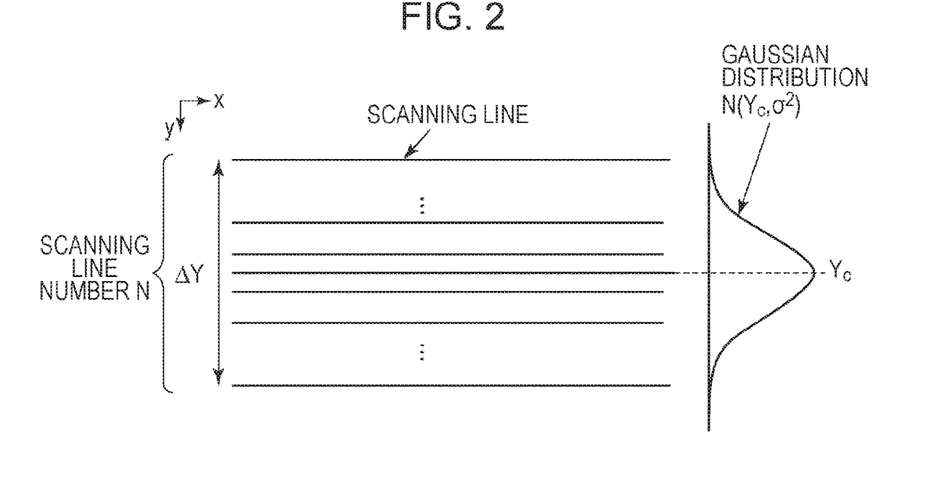
FIG. 2 is a diagram schematically illustrating a scanning pattern of a light interference tomographic image obtaining unit according to this embodiment.

A method for determining scanning positions in this embodiment will now be described with reference to FIG. 2. FIG. 2 is a diagram illustrating a pattern of scanning performed on the fundus which is a target of obtainment of a plurality of tomographic images for generation of an averaged image. In FIG. 2, "N" denotes the number of scanning lines and "$Y_c$" denotes a position in which a tomographic image is to be obtained in a Y direction. Here, the position "$Y_c$" is an example of the first imaging position. The scanning pattern has a scanning width $\Delta Y$ including the position $Y_c$ at a center so that speckle noise is removed. The position $Y_c$ and the width $\Delta Y$ are set by the operator of the apparatus as described below. The width $\Delta Y$ is an example of an imaging range input by the user. The width $\Delta Y$ may be automatically determined using the technique disclosed in Japanese Patent Laid-Open No. 2011-95005. Furthermore, a characteristic portion (a macula, an optic papilla, a lesion, or the like) of the fundus may be detected by analyzing a fundus image so that the scanning position $Y_c$ is automatically determined. That is, the position $Y_c$ and the width $\Delta Y$ may be automatically or manually determined.

Furthermore, in order to reduce a blur of an averaged image in this embodiment, positions of individual scanning operations in the Y direction are determined such that a density distribution corresponds to a Gaussian distribution. Specifically, a plurality of imaging positions are determined such that intervals among the imaging positions are increased as the imaging positions are separated from the first imaging position.

A mean value of the Gaussian distribution matches the position $Y_c$, and a dispersion $\sigma^2$ thereof is determined in accordance with the value $\Delta Y$. N is preferably an odd number so that the numbers of scanning lines in opposite sides relative to the value $Y_c$ are the same as each other. However, the present invention is not limited to this. Positions of the scanning lines in the Y direction are denoted by $Y_i$ (i=0, 1, ... N−1). Furthermore, the position $Y_c$ is located in a center of the scanning pattern and is represented by the following relationship.

$$Y_c = Y_{\lfloor \frac{N-1}{2} \rfloor}$$

Figure 3:
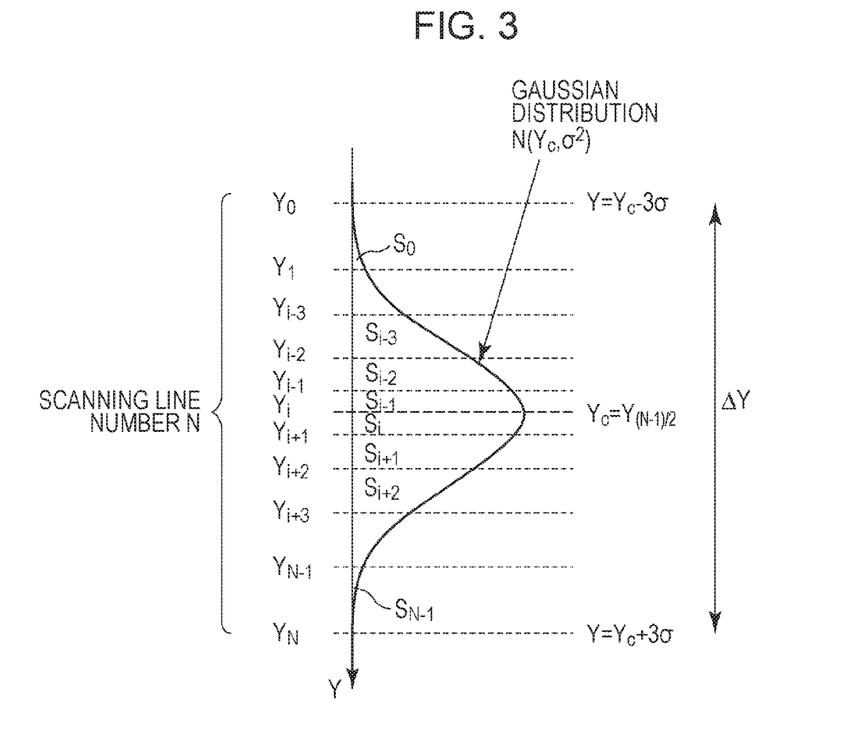
FIG. 3 is a diagram illustrating scanning positions of the light interference tomographic image obtaining unit according to this embodiment.

Next, a method for determining scanning positions in the Gaussian distribution will be described with reference to FIG. 3 while the position $Y_i$ is formulated.

In this embodiment, a scanning position of an i-th scanning line Yi is determined so as to be found in a range represented by "$Y=Y_0 \pm 3\sigma$", and the relationship between the width $\Delta Y$ and spread of the Gaussian distribution is represented by Expression (1).

$$\Delta Y = 6\sigma \quad \text{Expression (1)}$$

Then, assuming that areas of the Gaussian distribution divided by the scanning lines $Y_i$ are denoted by $S_i$ as represented by Expression (2), positions of the scanning lines $Y_i$ are determined such that N−1 areas $S_i$ are obtained by evenly dividing the area of the Gaussian distribution.

$$S_i = \frac{1}{N-1} \quad \text{Expression (2)}$$

It is assumed here that a probability density function of the scanning position corresponds to a Gaussian distribution represented by Expression (3).

$$f(Y_i) = \frac{1}{\sqrt{2\pi}\,\sigma} \exp\left\{\frac{-(Y_i - Y_c)^2}{2\sigma^2}\right\} \quad \text{Expression (3)}$$

Furthermore, a primitive function $F(Y_i)$ of the Gaussian function is represented as follows.

$$F(Y_i) = \int_{-\infty}^{Y_i} f(Y_i)\,dY = \frac{1}{2}\left\{1 + \text{erf}\left(\frac{Y_i - Y_c}{\sqrt{2}\,\sigma}\right)\right\} \quad \text{Expression (4)}$$

Here, "erf" denotes an error function of Gauss.

Expression (4) represents a cumulative distribution function of the entire Gaussian distribution, and a cumulative distribution function in the following range in the Gaussian distribution is represented by Expression (5) below, and is equal to an expression "$S_0 = S_1 + \ldots + S_{i-1}$" according to FIG. 3.

$$Y_0 \leq Y_i \leq Y_N$$

Therefore, the following expression is obtained.

$$\int_{Y_0}^{Y_i} f(Y_i)\,dY = \quad \text{Expression (5)}$$

$$\frac{1}{2}\left\{\text{erf}\left(\frac{Y_i - Y_c}{\sqrt{2}\,\sigma}\right) + \text{erf}\left(\frac{3}{\sqrt{2}}\right)\right\} = S_0 + S_1 + \ldots + S_{i-1}$$

Here, as described above, since positions of the scanning lines $Y_i$ are determined such that all areas Si are obtained by evenly dividing the area of the Gaussian distribution, that is, 1, the following relationship is satisfied according to Expression (2).

$$S_0 + S_1 + \ldots + S_{i-1} = \frac{i}{N-1} \quad \text{Expression (6)}$$

Therefore, the following expression is obtained according to Expressions (5) and (6).

$$\frac{1}{2}\left\{\text{erf}\left(\frac{Y_i - Y_c}{\sqrt{2}\,\sigma}\right) + \text{erf}\left(\frac{3}{\sqrt{2}}\right)\right\} = \frac{i}{N-1} \quad \text{Expression (7)}$$

When Expression (7) is solved for the value $Y_i$, the position of the i-th scanning line $Y_i$ may be represented by the following expression.

$$Y_i = Y_c + \sqrt{2}\,\sigma\mathrm{erf}^{-1}\!\left(\frac{2i}{N-1} - \mathrm{erf}\!\left(\frac{3}{\sqrt{2}}\right)\right),$$ Expression (8)

$$0 \le i \le N-1$$

Although the scanning lines $Y_i$ are obtained by calculation in this embodiment, the scanning lines $Y_i$ may be given by a computer as normal random numbers of $N(Y_c, \sigma^2)$.

Here, when a distribution σ of the scanning pattern on the target fundus is to be obtained, an error caused by a movement of an eye at a time of tracking is taken into consideration in practice. Accordingly, assuming that a distribution of scanning obtained by meaningly moving a position of scanning of the light interference tomographic image obtaining unit 3 is denoted by $\sigma_s^2$ and a distribution caused by a movement of an eye at the time of tracking is denoted by $\sigma_e^2$, the following relationship is satisfied due to additivity of distributions: $\sigma^2 = \sigma_s^2 + \sigma_e^2$, (Expression (9)). In this embodiment, the distribution σ is determined in accordance with Expression (1) when the user inputs the value ΔY, the tracking error estimation unit 534 determines the tracking error a e, and the scanning position calculation unit 535 determines the distribution $\sigma_s$ in accordance with Expression (9).

Concrete Processing Procedure

Figure 4:
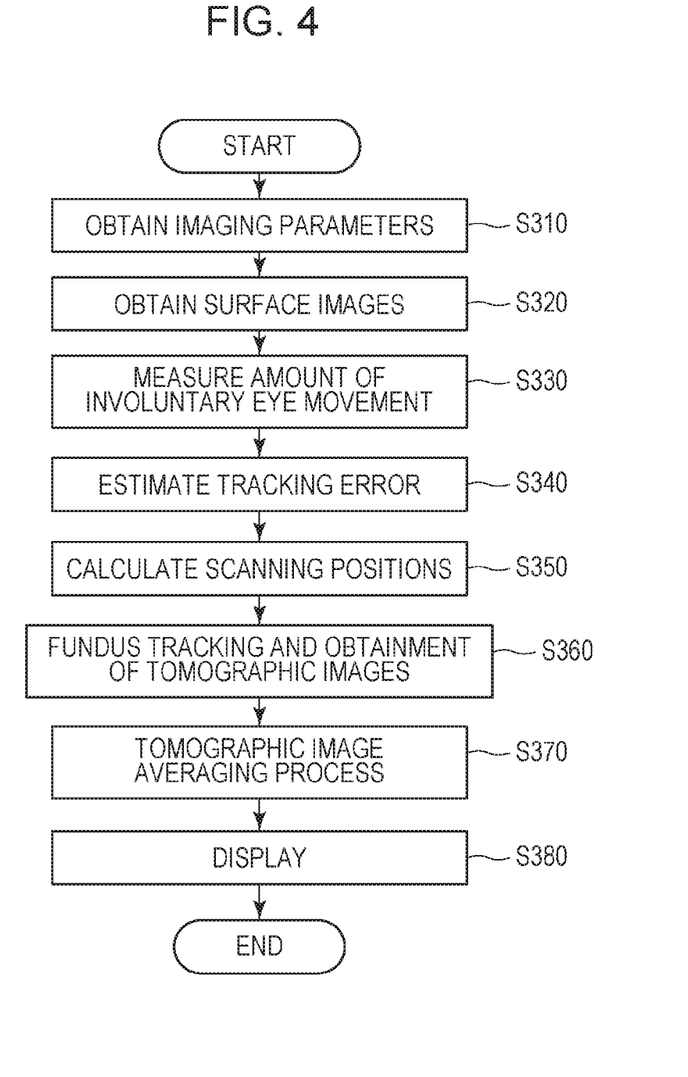
FIG. 4 is a flowchart illustrating a processing procedure according to this embodiment.

Next, a procedure of processing of the ophthalmologic apparatus 1 according to this embodiment will be described in detail with reference to FIG. 4.

Step S310

In step S310, when the operator performs an input using a mouse, a keyboard, or the like, the imaging parameter obtaining unit 538 obtains parameters used to determine a scanning pattern on the fundus which is a target for obtaining a plurality of tomographic images used to generate an averaged image. Specifically, the imaging parameter obtaining unit 538 obtains the scanning position $Y_c$, the scanning width ΔY, and the number N of scanning lines.

Note that the scanning width ΔY may correspond to a width of speckle noise calculated from a wavelength of a laser. Furthermore, a small width ΔY may be set when a lesion or an imaging target is small whereas a large width ΔY may be set when a lesion or an imaging target is large.

Step S320

In step S320, the driving controller 523 requests the surface image obtaining unit 2 to capture surface images of the subject's eye and transmit the obtained images so as to cause the surface image obtaining unit 2 to capture the surface images of the subject's eye. Furthermore, when receiving the surface images of the subject's eye captured by the surface image obtaining unit 2, the driving controller 523 transmits the surface images to the involuntary-eye-movement-amount measurement unit 533. Note that the surface image obtaining unit 2 may directly transmit the captured surface images to the involuntary-eye-movement-amount measurement unit 533.

Step S330

In step S330, the involuntary-eye-movement-amount measurement unit 533 displays the fixation lamp unit 6 so that the subject's eye fixates on the fixation lamp unit 6. Meanwhile, the involuntary-eye-movement-amount measurement unit 533 consecutively obtains frames of the surface images from the surface image obtaining unit 2 so as to measure an amount of an involuntary eye movement by performing the signal processing. The obtained amount of an involuntary eye movement is transmitted to the tracking error estimation unit 534. The process of measuring an amount of an involuntary eye movement will be described in detail later. Note that the involuntary-eye-movement-amount measurement unit 533 may cause the fixation lamp unit 6 to display the fixation lamp to the subject's eye in step S320.

Step S340

In step S340, the tracking error estimation unit 534 estimates the tracking error $\sigma_e$. The tracking error $\sigma_e$ indicates an amount of a movement of the fundus in a period of time from a time point when the surface image obtaining unit 2 obtains a surface image to when the X-Y scanning mirror 511 of the light interference tomographic image obtaining unit 3 is driven after the fundus tracking control unit 537 performs template comparison and detects a fundus position (hereinafter referred to as a tracking delay). Specifically, the tracking error $\sigma_e$ is an example of a value corresponding to a difference between the first imaging position which is controlled by the tracking unit so as to track the predetermined position of the eye portion and the predetermined position.

In this embodiment, the fundus tracking control unit 537 performs the fundus tracking such that the tracking delay is substantially equal to a cycle for obtaining a surface image. Here, the tracking error $\sigma_e$ is obtained as follows.

Figure 5:
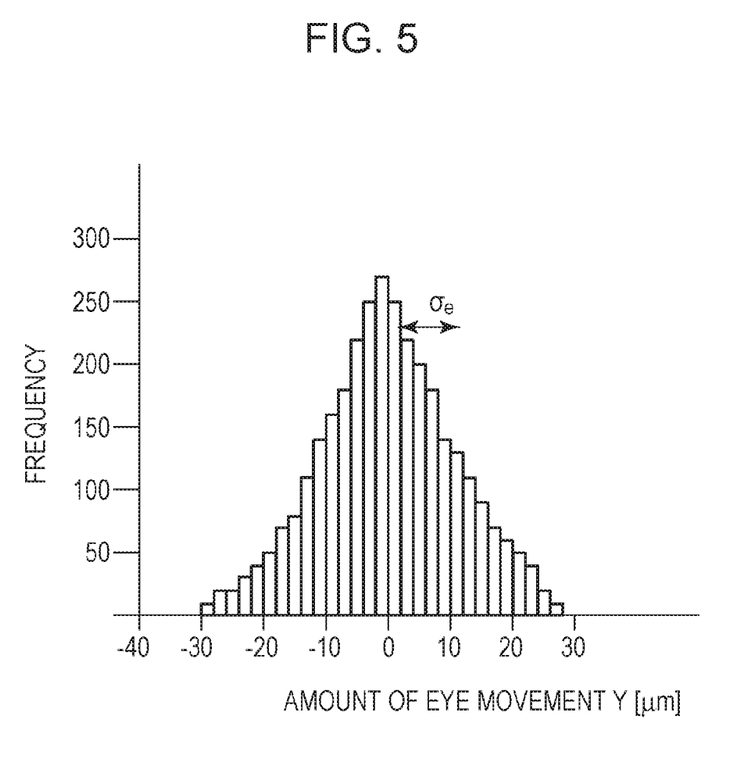
FIG. 5 is a graph illustrating a frequency distribution of an amount of fundus movement for one frame in detail.

A difference between a fundus position of a certain frame and a fundus position of a preceding frame (hereinafter referred to as an "each-frame fundus movement amount") is obtained for each frame of the surface images in accordance with the amount of an involuntary eye movement obtained by the involuntary-eye-movement-amount measurement unit 533 in step S330. Specifically, the involuntary-eye-movement-amount measurement unit 533 which is an example of a detection unit compares the plurality of frames of the surface images with each other so as to detect a movement of the subject's eye. A distribution calculated by the each-frame fundus movement amounts is indicated by a tracking error $\sigma_e^2$. The number of each-frame fundus movement amounts is obtained by subtracting 1 from the number of image frames obtained in the involuntary-eye-movement amount measurement. A frequency distribution of the each-frame fundus movement amount is illustrated in FIG. 5 in detail.

Step S350

In step S350, the scanning position calculation unit 535 calculates scanning positions (hereinafter denoted by "Ys") of the light interference tomographic image obtaining unit 3. As with the target scanning pattern, the scanning positions Ys are represented by the Gaussian distribution.

First, a standard deviation $\sigma_s$ of a scanning position of the light interference tomographic image obtaining unit 3 is obtained by Expression (10).

$$\sigma_s = \sqrt{\sigma^2 - \sigma_e^2}$$ Expression (10)

Here, the distribution σ has been obtained according to Expression (1) and the value $\sigma_e$ has been obtained in step S340, and therefore, the distribution $\sigma_s$ is obtained. Subsequently, the scanning position Ys is obtained by assigning the distribution $\sigma_s$ to Expression (8) instead of the distribution σ. Specifically, an i-th scanning position in the scanning positions Ys is determined as represented by Expression (11). Here, the scanning positions Ys other than the position $Y_c$ are examples of second imaging positions. That is, the second imaging positions represent a plurality of imaging positions. As is apparent from Expression (10), the scanning position calculation unit 535 reduces shift amounts $\sigma_s$ of shifts between the first imaging position and the second imaging positions as the values $\sigma_e$ indicating differences are large. Here, the value "α" is determined in accordance with the imaging range ΔY input by the user. That is, the value $\sigma_s$ is determined in accordance with the imaging range input by the user and a value corresponding to the error.

$$Y_{S_i} = Y_c + \sqrt{2}\,\sigma_s \text{erf}^{-1}\left(\frac{2i}{N-1} - \text{erf}\left(\frac{3}{\sqrt{2}}\right)\right), \quad \text{Expression (11)}$$

$$0 \le i \le N-1$$

As described above, the scanning position calculation unit 535 calculates the scanning position density distribution $\sigma_s$ of the target scanning pattern taking an error of an eye movement at a time of tracking into consideration. Then, the scanning positions Ys of the light interference tomographic image obtaining unit 3 are calculated in accordance with the distribution $\sigma_s$. Specifically, the scanning position calculation unit 535 is an example of a determination unit which determines a position shifted from the first imaging position which tracks the predetermined position as the second imaging position in accordance with a value corresponding to the error.

Note that, in a case where the distribution $\sigma_s$ is a negative value in Expression (10), a standard deviation caused by the tracking error is larger than a standard deviation of a final scanning pattern since an amount of an involuntary eye movement is large.

Therefore, the scanning line distribution $\sigma_s^2$ is set to 0 and scanning on the same line is repeatedly performed. Specifically, in a case where a value representing an error is larger than a predetermined value, an amount of shift between the first and second imaging positions is set to 0. Note that, since a blur may occur in an averaged image in this case, the scanning position calculation unit 535 displays an alert lamp representing a tracking error in the display unit 526. This alert lamp is useful for the operator to determine whether a light interference tomographic image is to be obtained again.

Step S360

In step S360, the fundus tracking control unit 537 executes the fundus tracking and the light interference tomographic image obtaining unit 3 obtains a plurality of tomographic images. Specifically, the light interference tomographic image obtaining unit 3 is an example of a tomographic image obtaining unit which obtains tomographic images in the first and second imaging positions. The fundus tracking and the obtainment of tomographic images will be described in detail hereinafter.

Step S370

In step S370, the tomographic image averaging unit 536 performs positioning on a plurality of tomographic images corresponding to the plurality of scanning lines output from the differential detector 571 of the light interference tomographic image obtaining unit 3 and averages pixel values so as to form an averaged tomographic image. Specifically, the tomographic image averaging unit 536 is an example of a generation unit which generates a tomographic image by averaging a plurality of tomographic images obtained by the tomographic image obtaining unit. The tomographic image averaging process will be described in detail hereinafter.

Step S380

In step S380, the display unit 526 displays the averaged tomographic image generated by the signal processing unit 524, the surface image, the number of times scanning is performed N, the number of images subjected to averaging, an image averaging threshold value, and the alert lamp representing the tracking error. Furthermore, the final scanning pattern is displayed on the surface image in a superimposing manner.

Figure 6:
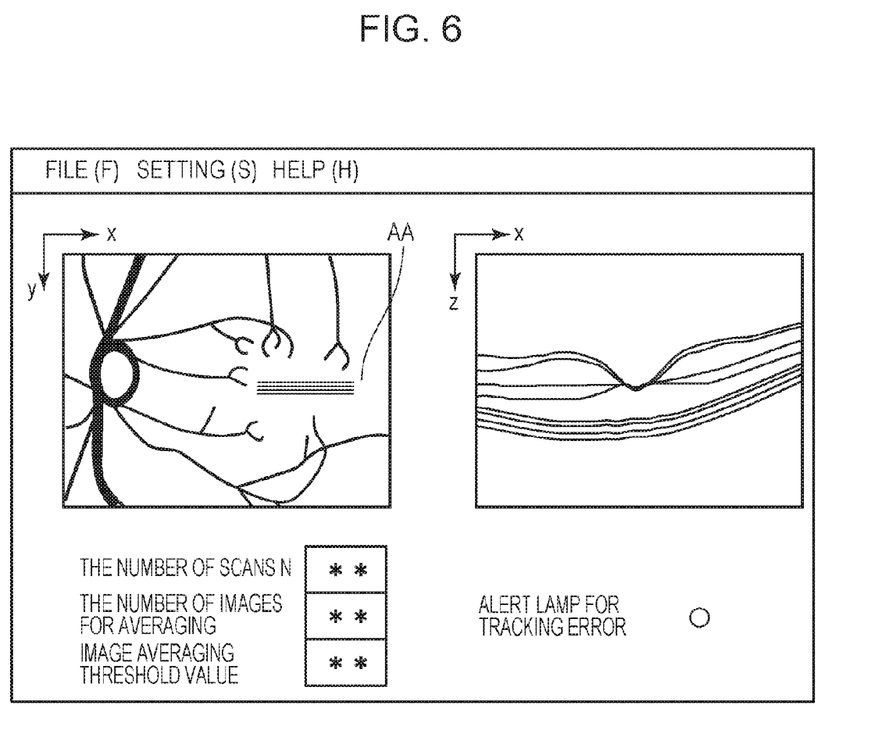
FIG. 6 is a diagram illustrating display in a display screen of a display unit included in an image processing apparatus according to this embodiment.

FIG. 6 is a diagram illustrating the display performed by the display unit 526.

Since a final scanning pattern AA is superimposed on the surface image, the operator may reliably recognize an imaging position of a tomographic image.

Process by Involuntary-Eye-Movement-Amount Measurement Unit

Figure 7:
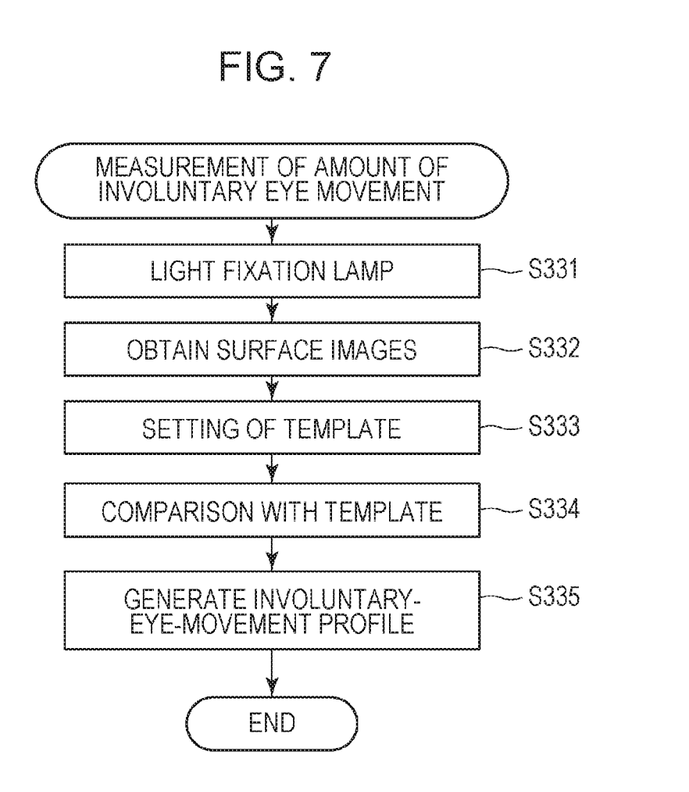
FIG. 7 is a flowchart illustrating a processing procedure according to this embodiment.

Next, a procedure of the involuntary-eye-movement amount measurement executed in step S330 will be described with reference to FIG. 7. In this embodiment, the surface images of the fundus are captured for a certain period of time while the examinee fixates so as to check a movement of the fundus. In this way, an amount of the involuntary eye movement of the subject's eye is measured.

Step S331

In step S331, the involuntary-eye-movement-amount measurement unit 533 instructs the driving controller 523 to light the fixation lamp so that the subject's eye fixates on the fixation lamp.

Step S332

In step S332, the involuntary-eye-movement-amount measurement unit 533 instructs the driving controller 523 to cause the surface image obtaining unit 2 to consecutively obtain surface images for 10 seconds at a rate of 30 Hz while the subject's eye fixates on the fixation lamp.

Step S333

In step S333, the involuntary-eye-movement-amount measurement unit 533 sets a leading one of the plurality of surface images obtained in step S332 as a template. The obtained template is stored in the data storage unit 525.

Note that, as the setting of the template, the operator may specify a template position in the surface image. In this case, it is preferable that a partial image of a characteristic portion, such as an intersection of fundus blood vessels, is extracted and set as a template. Since a portion template is used, a speed of a template comparison process to be executed later may be improved.

Note that the specifying of a position of the portion template may be automatically performed by the involuntary-eye-movement-amount measurement unit 533. In this case, a corner detection algorithm of Harris may be used as an algorithm for selecting an area including a characteristic pattern.

Note that a corner detection algorithm of Moravec or other corner detection algorithms may be used as the algorithm for selecting an area including a characteristic pattern.

Step S334

In step S334, the involuntary-eye-movement-amount measurement unit 533 compares the plurality of surface images obtained in step S332 with the template for each frame so as to obtain position shifting amounts (δX, δY, δθ).

Specifically, the involuntary-eye-movement-amount measurement unit 533 calculates normalized cross-correlation (NCC) which is an index indicating a degree of similarity while a position of a template image is shifted, and determines a difference between image positions in which a value of the NCC becomes maximum as a position shifting amount.

Note that any type of index may be used for representing a degree of similarity as long as the index represents a degree of similarity between a characteristic of an image included in a template and a characteristic of an image included in a frame. For example, the sum of absolute difference (SAD), the sum of squared difference (SSD), the zero-means normalized cross-correlation (ZNCC), or the like may be used.

Step S335

Figure 8:
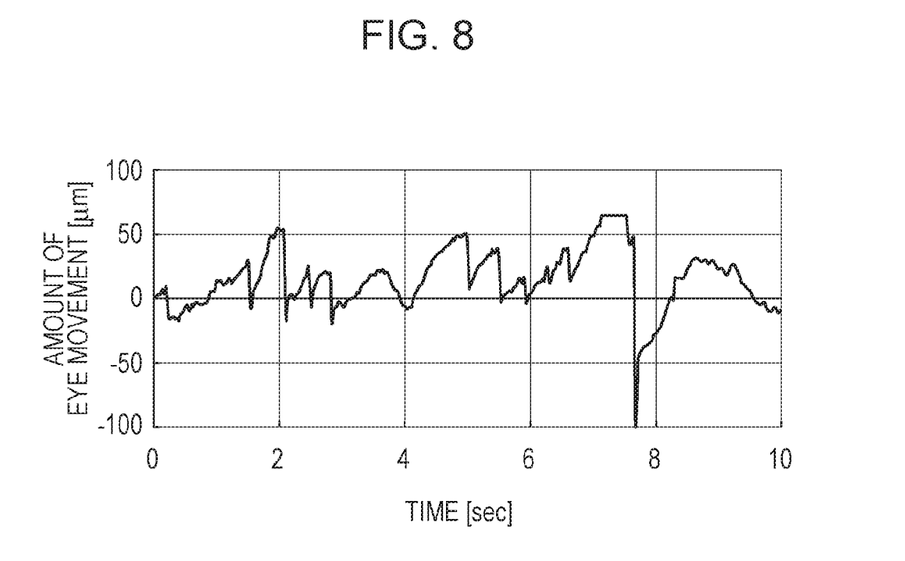
FIG. 8 is a diagram illustrating a result of involuntary-eye-movement amount measurement according to this embodiment.

In step S335, an amount of an involuntary eye movement in the Y direction is calculated by obtaining an amount of a movement of the template in a direction perpendicular to a scanning line (hereinafter referred to as a "movement in the Y direction") according to a result of the template comparison executed in step S334. A result of the measurement of the involuntary eye movement is illustrated in FIG. 8.

The amount of an involuntary eye movement is represented as a plot of eyeball positions for individual frames of the surface images in a graph in which an axis of ordinate represents an eyeball position and an axis of abscissa represents time.

Fundus Tracking and Obtainment of Tomographic Images

Next, a procedure of the fundus tracking and the obtainment of tomographic images executed in step S360 will be described with reference to FIG. 9.

Step S361

In step S361, the fundus tracking control unit 537 requests the surface image obtaining unit 2 to capture surface images of the subject's eye and transmit the obtained images so as to obtain 20 frames of surface images of the subject's eye for generation of a template. The obtained surface images are transmitted to the fundus tracking control unit 537.

Note that, although it is preferable that at least 20 frames of the surface images are obtained for the generation of a template, the numbers of frames is not limited to 20.

Step S362

In step S362, the fundus tracking control unit 537 averages the 20 frames of surface images obtained in step S361 so as to generate a tracking template.

Note that quality of a template image is improved as the number of surface images for the generation of the template is increased, and accordingly, accuracy of the template comparison is improved. However, if the number of surface images for the generation of the template is increased, a processing time required for the generation of the template is increased. Therefore, although the number of frames is determined taking required accuracy of the template comparison and a processing speed into consideration, it is preferable that the number of frames is 20 or more so that accuracy required for imaging of light interference tomographic images is ensured.

The fundus tracking control unit 537 stores the generated template image in the data storage unit 525.

Step S363

In step S363, the fundus tracking control unit 537 requests the surface image obtaining unit 2 to capture a surface image of the subject's eye and transmit the obtained image so as to obtain one frame of a surface image for tracking of the subject's eye. The obtained surface image is transmitted to the fundus tracking control unit 537.

Step S364

In step S364, the fundus tracking control unit 537 compares the template generated in step S362 with the surface image for tracking obtained in step S363 so as to calculate a fundus movement amount ($\delta X$, $\delta Y$, $\delta \theta$) of the surface image for tracking the template.

Note that detail of the template comparison is the same as that described in step S334, and therefore, a description thereof is omitted.

Step S365

In step S365, the fundus tracking control unit 537 drives the X-Y scanning mirror 511 so that a scanning position corresponds to the scanning position $Ys_i$ (refer to Expression (11)) calculated in step S350. Specifically, the tracking unit controls the scanning unit so that the first imaging position tracks the predetermined position. In this case, the fundus movement amount ($\delta X$, $\delta Y$, $\delta \theta$) calculated in step S364 is offset and the X-Y scanning mirror 511 is driven so that the scanning position follows a movement of the fundus.

Step S366

In step S366, the fundus tracking control unit 537 requests the light interference tomographic image obtaining unit 3 to capture a tomographic image of the subject's eye and transmit the obtained image so as to obtain a tomographic image of the subject's eye for one frame in one of N scanning positions calculated in step S350.

Figure 9:
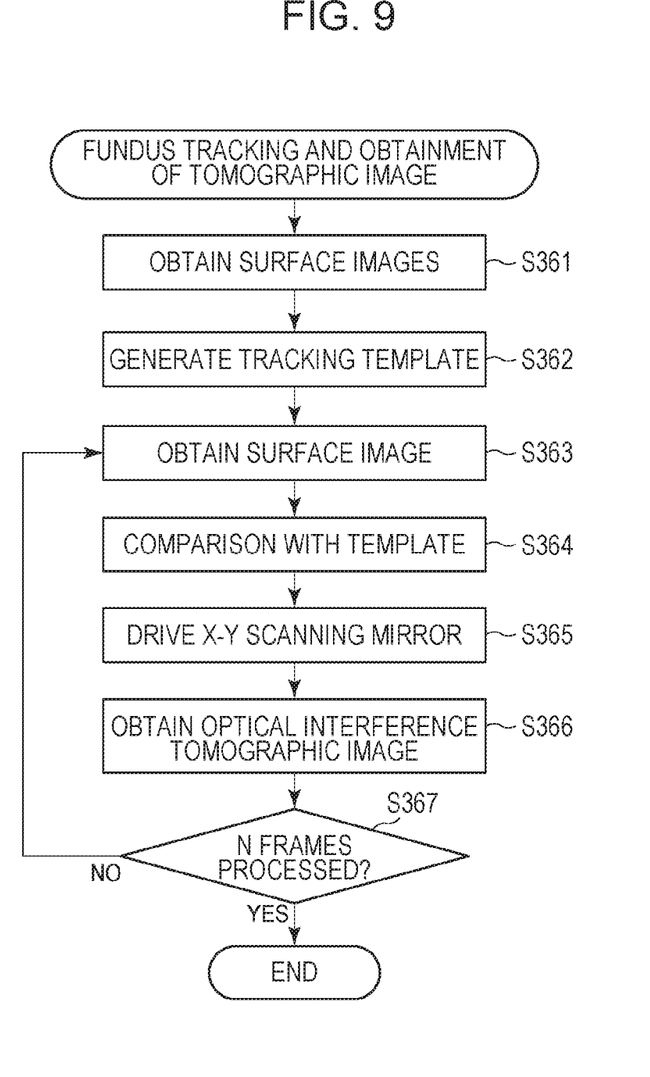
FIG. 9 is a flowchart illustrating a processing procedure according to this embodiment.

Furthermore, as represented by a repetitive operation in FIG. 9, the process from step S363 to step S366 is executed on the individual N scanning positions so that images for N frames are finally obtained (S367).

Here, a distribution of the final scanning pattern on the subject's eye is obtained by adding the tracking error $\sigma_e^2$ obtained when the movement of the fundus of the subject's eye is tracked to the scanning pattern distribution $\sigma_s^2$ calculated by the scanning position calculation unit 535, and a target scanning pattern distribution $\sigma$ represented by Expression (9) is realized.

Specifically, even if an involuntary eye movement is large, the subject's eye may be scanned using the scanning pattern having the scanning width $\Delta Y$ obtained by the imaging parameter obtaining unit 538 in step S310.

Tomographic Image Averaging Process

Figure 10:
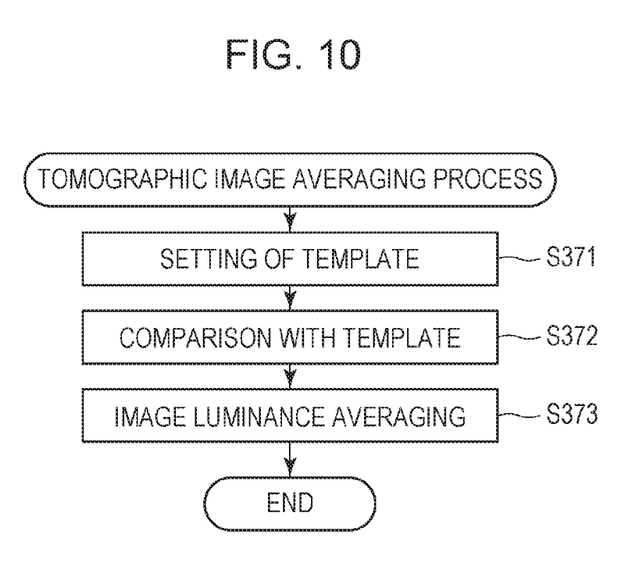
FIG. 10 is a flowchart illustrating a processing procedure according to this embodiment.

Next, a procedure of the tomographic image averaging process executed in step S370 will be described with reference to FIG. 10.

Step S371

In step S371, the tomographic image averaging unit 536 calculates luminance correlations of all combinations of the N frames of the tomographic images generated in step S360 and determines one of the frames having a largest sum of correlation coefficients with other images as a template image. By this, an image having a smallest blur caused by the involuntary eye movement may be used as a template.

Alternatively, among the tomographic images for N frames, a tomographic image corresponding to a center scanning position may be selected as a template image so that the center scanning position is accurately obtained by averaging.

Step S372

In step S372, the template image selected in step S371 is compared with images of N-1 frames which are other than the template image.

Then images having correlation coefficients obtained at the time of the template comparison which are equal to or larger than a threshold value are extracted. By this, the averaging may be performed without using images having large blurs.

Since the light interference tomographic images are obtained while position control is performed by tracking in this embodiment, a larger number of images are extracted when compared with a case where tracking is not performed, and accordingly, the obtained images may be efficiently averaged.

Note that detail of the template comparison is the same as that described in step S334, and therefore, a description thereof is omitted.

Step S373

In step S373, positioning is performed on the images extracted in step S372 and luminance values are averaged in individual pixels so that an averaged tomographic image is generated.

As described above, in this embodiment, an amount of an involuntary eye movement is measured, a tracking error is estimated in accordance with the amount of the involuntary eye movement so that scanning positions for obtaining light interference tomographic images are determined, and the light interference tomographic images are obtained while tracking is performed. Accordingly, an ophthalmologic apparatus capable of reducing a blur of an image by averaging a plurality of light interference tomographic images and effectively reducing speckle noise even in a case where the involuntary eye movement of the subject is large may be realized. Specifically, the reduction of the speckle noise included in the tomographic images and reduction of the blurs of the tomographic images may be simultaneously realized.

Other Embodiments

Additional embodiment(s) can also be realized by a computer of a system or apparatus that reads out and executes computer executable instructions recorded on a storage medium (e.g., non-transitory computer-readable storage medium) to perform the functions of one or more of the above-described embodiments of the present invention, and by a method performed by the computer of the system or apparatus by, for example, reading out and executing the computer executable instructions from the storage medium to perform the functions of one or more of the above-described embodiments. The computer may comprise one or more of a central processing unit (CPU), micro processing unit (MPU), or other circuitry, and may include a network of separate computers or separate computer processors. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present disclosure has been described with reference to exemplary embodiments, it is to be understood that these exemplary embodiments are not seen to be limiting. The scope of the following claims is to be accorded the broadest interpretation so as to encompass all such modifications and equivalent structures and functions.

This application claims the benefit of Japanese Patent Application No. 2014-254597, filed Dec. 16, 2014, which is hereby incorporated by reference herein in its entirety.

What is claimed is:

1. An ophthalmologic apparatus comprising:
a detection unit configured to detect a movement amount of a subject's eye;
an error obtaining unit configured to obtain a value of tracking error based on a result of the detection;
a determining unit configured to determine each position of a plurality of scanning lines at intervals corresponding to the value of tracking error;
a tomographic image obtaining unit configured to obtain a plurality of tomographic images by scanning each position of the plurality of scanning lines with measurement light; and
a generation unit configured to generate an averaged tomographic image by averaging pixel values of the plurality of tomographic images obtained by the tomographic image obtaining unit,
wherein the determining unit determines the intervals based on the value of tracking error.

2. The ophthalmologic apparatus according to claim 1, wherein
the determining unit reduces the intervals as the value of tracking error increases.

3. The ophthalmologic apparatus according to claim 2, wherein
the determining unit determines the intervals to 0 when the value of tracking error is larger than a predetermined value.

4. The ophthalmologic apparatus according to claim 3, wherein
the tomographic image obtaining unit is optical coherence tomography (OCT) including a scanning unit, and
the scanning line is corrected by controlling the scanning unit.

5. The ophthalmologic apparatus according to claim 2, wherein
the tomographic image obtaining unit is optical coherence tomography (OCT) including a scanning unit, and
the scanning line is corrected by controlling the scanning unit.

6. The ophthalmologic apparatus according to claim 1, further comprising:
a surface image obtaining unit configured to obtain a surface image of the subject's eye,
wherein the detection unit detects the movement amount of the subject's eye by comparing a plurality of surface images.

7. The ophthalmologic apparatus according to claim 6, wherein
the determining unit determines each position of the plurality of scanning lines such that the intervals become larger as the scanning lines are more distant from a center of the plurality of scanning lines.

8. The ophthalmologic apparatus according to claim 7, wherein
the tomographic image obtaining unit is optical coherence tomography (OCT) including a scanning unit, and
the scanning line is corrected by controlling the scanning unit.

9. The ophthalmologic apparatus according to claim 6, wherein
the tomographic image obtaining unit is optical coherence tomography (OCT) including a scanning unit, and
the scanning line is corrected by controlling the scanning unit.

10. The ophthalmologic apparatus according to claim 1, wherein
the determining unit determines each position of the plurality of scanning lines such that the intervals become larger as the scanning lines are more distant from a center of the plurality of scanning lines.

11. The ophthalmologic apparatus according to claim 10, wherein
the tomographic image obtaining unit is optical coherence tomography (OCT) including a scanning unit, and
the scanning line is corrected by controlling the scanning unit.

12. The ophthalmologic apparatus according to claim 1, wherein the tomographic image obtaining unit is optical coherence tomography (OCT) including a scanning unit, and the scanning line is corrected by controlling the scanning unit.

13. The ophthalmologic apparatus according to claim 1, wherein the determining unit determines a width of an imaging region in accordance with an imaging range input by a user and the value of tracking error.

14. A tomographic image generation method comprising:

detecting a movement amount of a subject's eye;

obtaining a value of tracking error based on a result of the detecting;

determining each position of a plurality of scanning lines at intervals corresponding to the value of tracking error;

obtaining a plurality of tomographic images by scanning each position of the plurality of scanning positions lines with measurement light; and generating an averaged tomographic image by averaging pixel values of the plurality of tomographic images obtained by the obtaining, wherein determining determines the intervals based on the value of tracking error.

15. A non-transitory computer-readable storage medium storing computer executable instructions for causing a computer to execute a tomographic image generation method comprising:

detecting a movement amount of a subject's eye;

obtaining a value of tracking error based on a result of the detecting;

determining each position of a plurality of scanning positions on lines at intervals corresponding to the value of tracking error;

obtaining a plurality of tomographic images by scanning each position of the plurality of scanning lines with measurement light; and generating an averaged tomographic image by averaging pixel values of the plurality of tomographic images obtained by the obtaining, wherein determining determines the intervals based on the value of tracking error.

* * * * *